US007069069B2

(12) United States Patent
Fishler et al.

(10) Patent No.: US 7,069,069 B2
(45) Date of Patent: Jun. 27, 2006

(54) IMPLANTABLE CARDIAC DEVICE FOR AND METHOD OF MONITORING PROGRESSION OR REGRESSION OF HEART DISEASE BY QUANTIFYING MORPHOLOGICAL FEATURES

(75) Inventors: Matthew G. Fishler, Sunnyvale, CA (US); Eric Falkenberg, Simi Valley, CA (US); Drew Hoffmann, Santa Clara, CA (US)

(73) Assignee: Pacesetter, Inc., Sylmar, CA (US)

( * ) Notice: Subject to any disclaimer, the term of this patent is extended or adjusted under 35 U.S.C. 154(b) by 197 days.

(21) Appl. No.: 10/094,929

(22) Filed: Dec. 6, 2001

(65) Prior Publication Data

US 2005/0033368 A1 Feb. 10, 2005

Related U.S. Application Data

(63) Continuation of application No. 09/487,858, filed on Jan. 19, 2000, now abandoned.

(51) Int. Cl.
*A61B 5/0472* (2006.01)

(52) U.S. Cl. ...................... 600/513; 600/516; 600/517; 600/521

(58) Field of Classification Search ...................... None
See application file for complete search history.

(56) References Cited

U.S. PATENT DOCUMENTS

| 5,817,134 A | * | 10/1998 | Greenhut et al. | 607/14 |
| 6,129,744 A | | 10/2000 | Boute | 607/25 |
| 6,324,427 B1 | * | 11/2001 | Florio | 607/28 |

FOREIGN PATENT DOCUMENTS

| EP | 0472411 A1 | 2/1992 |
| EP | 0554208 A2 | 8/1993 |
| EP | 0920885 A1 | 6/1999 |
| WO | WO 99/30777 | 6/1999 |
| WO | WO 99/58056 | 11/1999 |

* cited by examiner

*Primary Examiner*—Kennedy Schaetzle (57) ABSTRACT

An implantable cardiac device and method provides for monitoring a progression or regression in heart disease during an extended time period. A sensor generates an electrogram signal representing electrical activity of a patient's heart. From the generated electrogram signal, a processor determines morphology measurements wherein the morphology measurements indicate a progression or regression in the heart disease. The morphology measurements are stored in a memory during the extended period of time. A telemetry circuit transmits the stored morphology measurements to an external receiver for retrieval or display. The morphology measurements may be of electrogram intrinsic activity or evoked response activity characteristics.

30 Claims, 4 Drawing Sheets

IMPLANTABLE CARDIAC DEVICE FOR AND METHOD OF MONITORING PROGRESSION OR REGRESSION OF HEART DISEASE BY QUANTIFYING MORPHOLOGICAL FEATURES

FIELD OF THE INVENTION

The present invention is generally directed to an implantable device for monitoring the progression or regression of heart disease. The present invention is more particularly directed to such a device which extracts and quantifies morphological features from an electrogram signal representing electrical activity of a patient's heart over an extended time period, the morphological features being indicative of the progression or regression of the heart disease.

BACKGROUND OF THE INVENTION

More people die of heart disease than any other single cause. One common form of heart disease is congestive heart failure.

Congestive heart failure (CHF) is a debilitating, end-stage disease in which abnormal function of the heart leads to inadequate bloodflow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Only an option in 1 out of 200 cases, heart transplantation is also available. Other cardiac surgery is also indicated for only a small percentage of patients with particular etiologies. Although advances in pharmacological therapy have significantly improved the survival rate and quality of life of patients, patients who are refractory to drug therapy, have a poor prognosis and limited exercise tolerance. Cardiac pacing has been proposed as a new primary treatment for patients with drug-refractory CHF.

By tracking the progression or regression of heart disease, such as CHF, more closely, treatments could be managed more effectively. Commonly, patients with heart disease have an implanted cardiac stimulation device. Hence, it would be advantageous if the implanted cardiac stimulation device were able to aid in the tracking of the progression or regression of the heart disease. While some devices have been proposed to track a patient's heart condition, these devices have relied upon sensing activity and/or respiration of the patient. Unfortunately, this requires additional complexity to an already complex device. The present invention addresses the issues of tracking heart disease progression or regression by making use of an electrogram signal commonly available in implantable cardiac stimulation devices.

SUMMARY OF THE INVENTION

The present invention provides an implantable cardiac device for and method of detecting a progression or regression in heart disease such as congestive heart failure. A sensing circuit produces an electrogram signal indicative of the patient's heart activity. Degradation or improvement of the patient's condition over an extended time may be monitored from relative changes in morphology features or characteristics of the electrogram signal. A processor processes and evaluates the electrogram signal over the extended time by extracting and quantifying at least one morphology feature of selected cardiac cycles to determine morphology measurement data. A memory having a data storage area stores the morphology measurement data during the extended time and a telemetry circuit transmits the morphology measurement data to an external receiver for display.

The morphology measurement data are determined at frequent intervals to provide intermediate morphology measurement data. At less frequent intervals, such as once per day, final morphology measurement data is determined from the intermediate measurement data and stored in the memory. The morphology measurement data stored may, for example, represent a mean of, a variance in, an exponentially weighted average of, or an out-of-bound count or percent of the morphology characteristic.

The morphology feature or characteristic may be, for example, QRS duration or electrogram signal deflection polarity, area, or amplitude. The morphology measurement data may further be a mismatch score resulting from comparing selected cardiac cycle electrograms to a previously stored cardiac cycle electrogram. The morphology feature or characteristic may further be selected features of evoked responses.

BRIEF DESCRIPTION OF THE DRAWINGS

The above and other aspects, features, and advantages of the present invention will be more apparent from the following more particular description thereof presented in conjunction with the following drawings and wherein.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention may be used with various types of implantable cardiac devices, including implantable cardiac stimulation devices such as implantable pacemakers configured to treat bradycardia and/or tachycardia, or implantable cardioverter-defibrillators alone or combined with an implantable pacemaker, and implantable monitors.

To better understand the invention, it will first be helpful to have an understanding of the basic functions performed by the implantable stimulation device with which the invention is used, e.g., an implantable cardioverter-defibrillator (ICD) device and/or a dual-chamber pacemaker.

Figure 1:
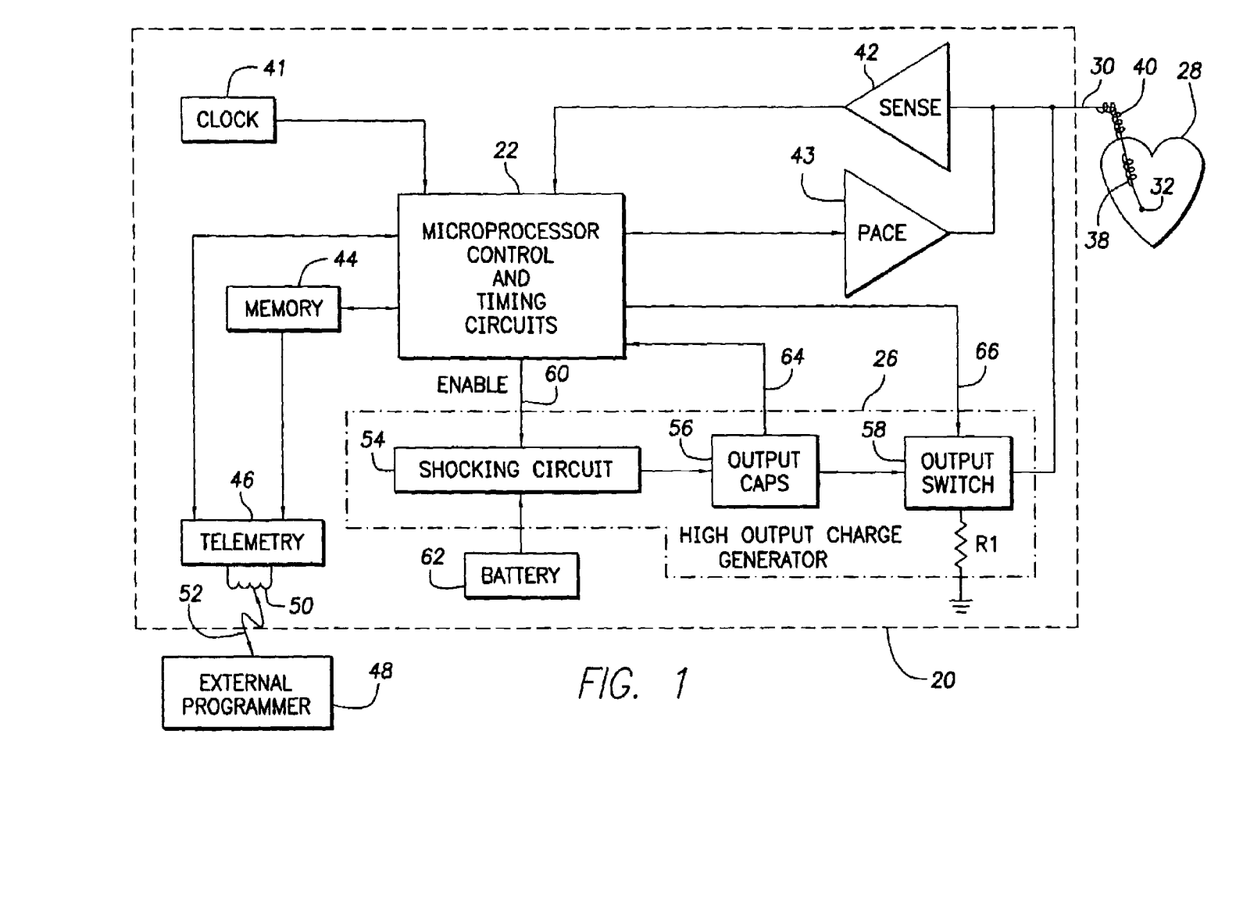
FIG. 1 shows a simplified functional block diagram of a combined implantable cardioverter/defibrillator and pacemaker (ICD), which represents one type of implantable stimulation device with which the present invention may be used.
Figure 2:
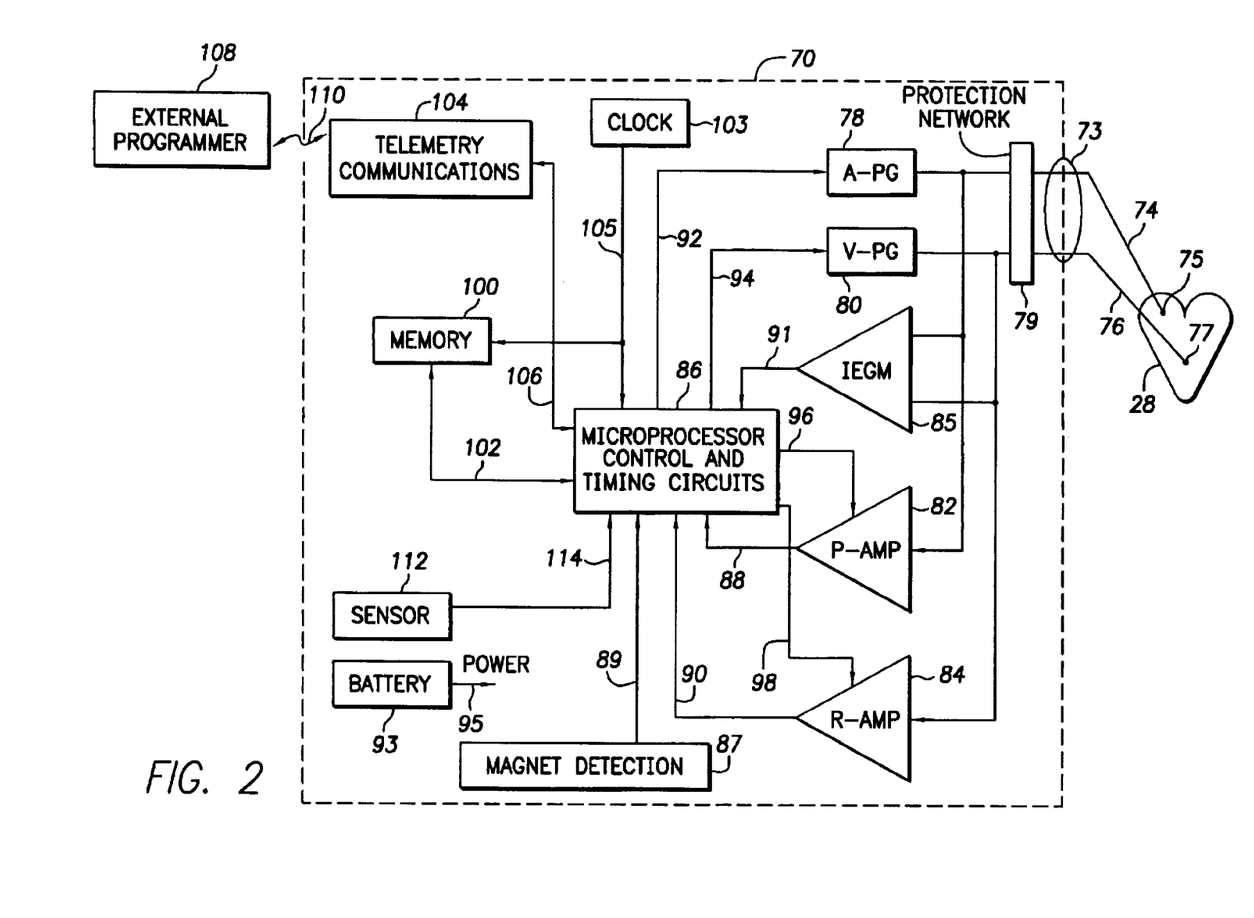
FIG. 2 is a functional block diagram of an implantable dual-chamber pacemaker, which represents another type of implantable medical device with which the invention may be used.

In FIG. 1, there is shown a simplified functional block diagram of an ICD device 20, and in FIG. 2, there is shown a simplified functional block diagram of a dual-chamber pacemaker 70. It should also be noted that the ICD 20 includes a pacing circuit 43 to combine the functionality of an ICD and a pacemaker within the same stimulation device.

It is the primary function of an ICD device to sense the occurrence of an arrhythmia, and to automatically apply an appropriate electrical shock therapy to the heart aimed at terminating the arrhythmia. To this end, the ICD device 20, as shown in the functional block diagram of FIG. 1, includes a control and timing circuit 22, such as a microprocessor, state-machine or other such control circuitry, that controls the ICD and pacemaker functions of the device 20.

With respect to the ICD function, a high output charge generator 26 is controlled by the circuit 22. The high output charge generator 26 generates electrical stimulation pulses of moderate or high energy (corresponding the cardioversion or defibrillation pulses, respectively), e.g., electrical pulses having energies of from 1 to 10 joules (moderate) or 11 to 40 joules (high), as controlled by the control/timing circuit 22.

Such moderate or high energy pulses are applied to the patient's heart through at least one lead 30 and between at least two defibrillation electrodes, such as coil electrodes 38 and 40 or between one electrode, such as electrode 38, and the device enclosure or case 20. The lead 30 preferably also includes at least one electrode for pacing and sensing functions, such as electrode 32. Typically, the lead 30 is transvenously inserted into the heart so as to place the coil electrodes 38 and 40 in the apex of the heart and in the superior vena cava, respectively. While only one lead is shown in FIG. 1, it is to be understood that additional defibrillation leads and electrodes may be used as desired or needed in order to efficiently and effectively apply the shock treatment generated by the high voltage generator 26 to the patient's heart 28.

The ICD 20 also includes a sense amplifier 42. It is the function of the sense amplifier 42 to sense the electrical activity of the heart 28 to generate an electrogram signal including, as is known in the art, R waves which occur upon the depolarization, and hence contraction, of ventricular tissue; and P waves which occur upon the depolarization, and hence contraction, of atrial tissue. Thus, by sensing R waves and/or P waves from the electrogram signal generated by the sense amplifier 42, the control/timing circuit 22 is able to make a determination as to the rate and regularity of the patient's heart beat and whether a pacing stimulation pulse should be delivered to the heart. Such information, in turn, also allows the control/timing circuit 22 to determine whether the heart 28 of a patient is experiencing a tachyarrhythmia, and to apply appropriate anti-tachyarrhythmia stimulation therapy. Further, as will be seen hereinafter, the electrogram signal is further utilized by the control/timing circuit 22 to extract and quantify at least one morphological characteristic to determine morphology measurements which may be used to track progression or regression of heart disease.

The control/timing circuit 22 further has a memory circuit 44 coupled thereto wherein the operating parameters and instructions used by the control/timing circuit 22 are stored. Such operating parameters define, for example, the amplitude of each shock energy pulse to be delivered to the patient's heart 28 within each tier of therapy, as well as the duration of these shock pulses. The operating instructions define the method steps performed by circuit 22 to implement the ICD and pacemaker functions. The memory 44 may take many forms, and may be subdivided into as many different memory blocks or sections (addresses) as needed to store desired data and control information. Such data may include the morphology measurements.

Advantageously, the operating parameters of the implantable device 20 may be non-invasively programmed into the memory 44 through a telemetry circuit 46, in telecommunicative contact with an external programmer 48 by way of a suitable coupling coil 50. The coupling coil 50 may serve as an antenna for establishing a radio frequency (RF) communication link 52 with the external programmer 48; or the coil 50 may serve as a means for inductively coupling data to and from the telemetry circuit 46 from and to the external programmer 48, as is known in the art. See, e.g., U.S. Pat. No. 4,809,697 (Causey, III et al.) and U.S. Pat. No. 4,944,299 (Silvian), incorporated herein by reference. Further, such telemetry circuit 46 advantageously allows status information relating to the operation of the ICD 20, as contained in the control/timing circuit 22 or memory 44, and the morphology measurements to be sent to the external programmer 48 through the established link 52 for retrieval.

The control/timing circuit 22 includes appropriate processing and logic circuits for analyzing the electrogram output of the sense amplifier 42 and determining if such signals indicate the presence of an arrhythmia. Typically, the control/timing circuit 22 is based on a microprocessor, or similar processing circuit, which includes the ability to process or monitor input signals (data) in a prescribed manner, e.g., as controlled by program code stored in a designated area or block of the memory 44. The details of the design and operation of the control/timing circuit 22 are not critical to the present invention. Rather, any suitable control/timing circuit 22 may be used that carries out the functions described herein. The use, design, and operation of microprocessor-based control circuits to perform timing and data analysis functions is known in the art.

The pacing pulse generator 43 may be of the type as described subsequently with respect to FIG. 2. It may provide for the delivery of pacing stimulation pulses to both the atria and ventricles. The control circuit 22, in analyzing the activity sensed by sensing circuit 42, provides for demand pacing. Only when there is an absence of natural R wave or P wave within an escape interval is a pacing pulse delivered.

In FIG. 2, a simplified block diagram of the circuitry needed for a dual-chamber pacemaker 70 is illustrated. The pacemaker 70 is coupled to a heart 28 by way of leads 74 and 76, the lead 74 having an electrode 75 that is in contact with one of the atria of the heart, and the lead 76 having an electrode 77 that is in contact with one of the ventricles of the heart. The leads 74 and 76 are electrically and physically connected to the pacemaker 70 through a connector 73 that forms an integral part of the housing wherein the circuits of the pacemaker are housed.

The connector 73 is electrically connected to a protection network 79, which network 79 electrically protects the circuits within the pacemaker 70 from excessive shocks or voltages that could appear on the electrodes 75 and/or 77 in the event such electrodes were to come in contact with a high voltage signal, e.g., from a defibrillation shock.

The leads 74 and 76 carry stimulating pulses to the electrodes 75 and 77 from an atrial pulse generator (A-PG) 78 and a ventricular pulse generator (V-PG) 80, respectively. Further, electrical signals from the atria are carried from the electrode 75, through the lead 74, to the input terminal of an atrial channel sense amplifier (P-AMP) 82; and electrical signals from the ventricles are carried from the electrode 77, through the lead 76, to the input terminal of a ventricular channel sense amplifier (R-AMP) 84. Hence, the amplifiers 82 and 84 each generates an electrogram signal. The electrogram signal of amplifier 82 contains mainly atrial activity of the heart and the electrogram signal of amplifier 84 contains mainly ventricular activity of the heart. Either one or both electrograms may be utilized for practicing the present invention.

Similarly, electrical signals from both the atria and ventricles are applied to the inputs of an IEGM (intracardiac electrogram) amplifier 85. The amplifier 85 is typically configured to detect an evoked response from the heart 28 in response to an applied stimulus, thereby aiding in the detection of "capture." (Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue.)

The dual-chamber pacemaker 70 is controlled by a control system 86 that typically includes a microprocessor programmed to carry out control and timing functions and morphology characteristic extraction and quantifying in accordance with the present invention. The control system 86 receives the electrogram signal from the atrial (P-AMP) amplifier 82 over signal line 88. Similarly, the control system 86 receives the electrogram signal from the ventricular (R-AMP) amplifier 84 over signal line 90, and the output signals from the IEGM amplifier 85 over signal line 91. These electrograms permit detection signals to be generated each time that a P wave or an R wave or an evoked response occurs within the heart 28. The control system 86 also generates trigger signals that are sent to the atrial pulse generator (A-PG) 78 and the ventricular pulse generator (V-PG) 80 over signal lines 92 and 94, respectively. These trigger signals are generated each time that a stimulation pulse is to be generated by the respective pulse generator 78 or 80. The atrial trigger signal is referred to simply as the "A-trigger," and the ventricular trigger signal is referred to as the "V-trigger."

During the time that either an A-pulse or V-pulse is being delivered to the heart, the corresponding amplifier, P-AMP 82 and/or R-AMP 84, is typically disabled by way of a blanking signal presented to these amplifiers from the control system over signal lines 96 and 98, respectively. This blanking action prevents the amplifiers 82 and 84 from becoming saturated from the relatively large stimulation pulses that are present at their input terminals during this time. This blanking action also helps prevent residual electrical signals present in the muscle tissue as a result of the pacemaker stimulation from being interpreted as P waves or R waves.

As shown in FIG. 2, the pacemaker 70 further includes a memory circuit 100 that is coupled to the control system 86 over a suitable data/address bus 102. This memory circuit 100 allows certain control parameters, used by the control system 86 in controlling the operation of the pacemaker, to be programmably stored and modified, as required, in order to customize the pacemaker's operation to suit the needs of a particular patient. Further, data, such as the morphology measurements, determined or sensed during the operation of the pacemaker may be stored in the memory 100 for later retrieval and analysis.

As with the memory 44 of the ICD device 20 shown in FIG. 1, the memory 100 of the pacemaker 70 (FIG. 2) may take many forms. It may be subdivided into as many different memory blocks or sections (addresses) as needed in order to allow desired data and control information to be stored.

A clock circuit 103 directs an appropriate clock signal(s) to the control system 86, as well as to any other needed circuits throughout the pacemaker 70 (e.g., to the memory 100) by way of clock bus 105.

A telemetry/communications circuit 104 is further included in the pacemaker 70. This telemetry circuit 104 is connected to the control system 86 by way of a suitable command/data bus 106. In turn, the telemetry circuit 104, which is included within the implantable pacemaker 70, may be selectively coupled to an external programming device 108 by means of an appropriate communication link 110, which communication link 110 may be any suitable electromagnetic link, such as an RF (radio frequency) channel, a magnetic link, an inductive link, an optical link, and the like. Advantageously, through the external programmer 108 and the communication link 110, desired commands may be sent to the control system 86. Similarly, through this communication link 110 with the programmer 108, data commands (either held within the control system 86, as in a data latch, or stored within the memory 100) may be remotely received from the programmer 108. Similarly, data initially sensed through the leads 74 or 76, and processed by the microprocessor control circuits 86, or other data, such as the morphology measurements, measured within or by the pacemaker 70, may be stored and uploaded to the programmer 108 for display. In this manner, non-invasive communications can be established with the implanted pacemaker 70 from a remote non-implanted, location.

The pacemaker 70 additionally includes a battery 93. The battery 93 provides operating power to all of the circuits of the pacemaker 70 via a POWER signal line 95.

It is noted that the pacemaker 70 in FIG. 2 is referred to as a dual-chamber pacemaker because it interfaces with both the atria and the ventricles of the heart. Those portions of the pacemaker 70 that interface with the atria, e.g., the lead 74, the P wave sense amplifier 82, the A-PG 78, and corresponding portions of the control system 86, are commonly referred to as the "atrial channel." Similarly, those portions of the pacemaker 70 that interface with the ventricles, e.g., the lead 76, the R wave sense amplifier 84, the V-pulse generator 80, and corresponding portions of the control system 86, are commonly referred to as the "ventricular channel."

The pacemaker 70 further includes an activity sensor 112 that is connected to the control system 86 of the pacemaker 70 over a suitable connection line 114. The sensor 112 may be of the type well known in the art.

The pacemaker 70 further includes magnet detection circuitry 87, coupled to the control system 86 over signal line 89. It is the purpose of the magnet detection circuitry 87 to detect when a magnet is placed over the pacemaker, which magnet may be used by a physician or other medical personnel to perform various reset functions of the pacemaker 70, and/or to signal the control system 86 that an external programmer 108 is in place to receive data from, or send data to, the pacemaker memory 100 or control system 86 through the telemetry communications circuits 104.

As with the ICD device 20 of FIG. 1, the telemetry or communications circuit 104 may be of conventional design, such as is described in U.S. Pat. No. 4,944,299, or as is otherwise known in the art. Similarly, the external programmer 108 may be of any suitable design known in the art, such as is described in U.S. Pat. No. 4,809,697. Likewise, the memory circuit 100, and the circuits utilized in the atrial and ventricular channels may all be of common design as is known in the pacing art. The present invention is not concerned with the details of the circuitry utilized for each of these pacing elements. Rather, it is concerned with the manner in which all of these pacing elements cooperate with each other in order to provide a particular pacing mode of operation. Such cooperation is controlled by the control system 86.

The control system 86 may be realized using a variety of different techniques and/or circuits. The preferred type of control system 86 is a microprocessor-based control system. It is noted, however, that the control system 86 could also be realized using a state machine. Indeed, any type of control circuit or system could be employed for the control system 86. The present invention is likewise not concerned with the details of the control systems 22 and 86. Rather, it is concerned with the end result achieved by the control system. That is, so long as the control system 86 controls the operation of the pacemaker (or other medical device) so that the desired functions are achieved as set forth herein, e.g., by following the steps described below in the flow chart of FIG. 5, it matters little what type of control system is used. Those of skill in the implantable medical device art, given the teachings presented herein, should thus be able to fashion numerous different types of control systems or circuits that achieve the desired device control.

Representative of the types of control systems that may be used with the invention is the microprocessor-based control system described in U.S. Pat. No. 4,940,052, entitled "Microprocessor Controlled Rate-Responsive Pacemaker Having Automatic Rate Response Threshold Adjustment." Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are incorporated herein by reference.

Figure 3:
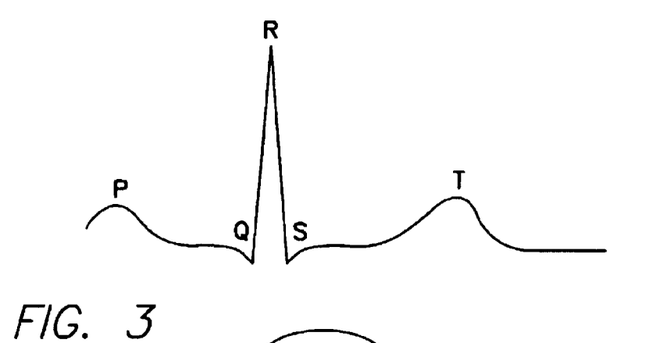
FIG. 3 is an electrogram illustrating a single cardiac cycle of a healthy heart.

Referring now to FIG. 3, it illustrates a typical or normal electrogram (EGM) illustrating the conventional nomenclature for a cardiac cycle of the heart. The beginning of the cardiac cycle is initiated by a P wave which is normally a small positive wave. It is the activation of the atria, forcing them to contract. Following the P wave there is an EGM portion which is substantially constant in amplitude. This substantially constant portion will have a time duration on the order of, for example, 120 milliseconds.

The QRS complex of the EGM then normally occurs after the substantially constant portion with a Q wave which is normally a small negative deflection which is immediately succeeded by the R wave which is a rapid positive deflection. The R wave generally has an amplitude greater than any other waves of the EGM signal and will have a spiked shape of relatively short duration with a sharp rise, a peak amplitude, and a sharp decline. The R wave may have a duration on the order of 40 milliseconds.

Following the R wave, the QRS complex is completed with an S wave. The S wave may be generally characterized by a small positive inflection in the EGM signal.

Following the S wave is the T wave. The T wave is relatively long in duration of, for example, on the order of 150 milliseconds. Following the T wave is a substantially constant amplitude until the next P wave occurs to begin the next cardiac cycle.

As CHF progresses, one or both of the atria enlarge. In addition, conduction speeds may decrease and become spatially, heterogeneous. The atrial electrogram complexes will then exhibit relative morphology changes in amplitude and area. Hence, an atrial electrogram may be used to track the progression or regression of the heart disease. For example, the amplitude of the P wave deflection will decrease over time as well as the area under the P wave deflection. These morphology characteristics may be extracted from the electrogram and quantified. When this procedure is implemented over time, the relative changes in the quantified morphology characteristic will provide an indication of the progression or regression of the heart disease.

To emphasize the sensed atrial activity and de-emphasize sensed ventricular activity, sensing electrode configurations are preferably used to capture as much atrial tissue and as little ventricular tissue as possible. Such sensing electrode configurations may be obtained by sensing between electrodes implanted in the right atrium and coronary sinus of the heart or by sensing between the conductive enclosure of the implanted device and an electrode implanted within either the right atrium or coronary sinus. The electrodes may be either the pace/sensing ring and tip type or less localized defibrillation coils. Any one of the foregoing sensing electrode configurations will provide an atrial electrogram suitable to support the extraction and quantifying of atrial deflection amplitudes or areas.

Similarly, as CHF progresses, the ventricles also enlarge and activation conduction speed decreases and activation heterogeneity increases. These changes are reflected in relative changes in ventricular morphology including decreases in deflection amplitude and area. For example, the R wave amplitude will decrease. The duration of the QRS complex will lengthen, and the area under the R wave deflections will decrease. The polarity of the R waves may even change. Hence, by tracking relative changes in any one or a combination of these morphology characteristics over time, the progression or regression of the heart disease may be monitored.

The changes in morphology may be further extracted and quantified by template matching, a technique well known in the art. A template of an electrogram cardiac cycle may be stored in memory. Periodically, later occurring electrogram cardiac cycles may be compared to the template. Alignment between the cardiac cycles may be accomplished by using fiducial points, a technique also well known in the art. Once aligned, the cardiac cycles, or complexes thereof, are compared. The comparison may be based upon area of corresponding deflections or amplitude of corresponding deflections. Further, the areas and amplitudes of recently sensed cardiac cycles may be assigned positive or negative values based upon the polarity of the corresponding deflections.

The foregoing comparison may be quantified by deriving, from the comparison, a mismatch score. The mismatch score may, for example, be expressed as a percentage, ranging between 0 and 1.00. A score of 100 percent represents a perfect match and a score of 0 percent represents a perfect mismatch. The mismatch score may be based upon comparative deflection amplitudes, areas, and polarity.

Figure 4:
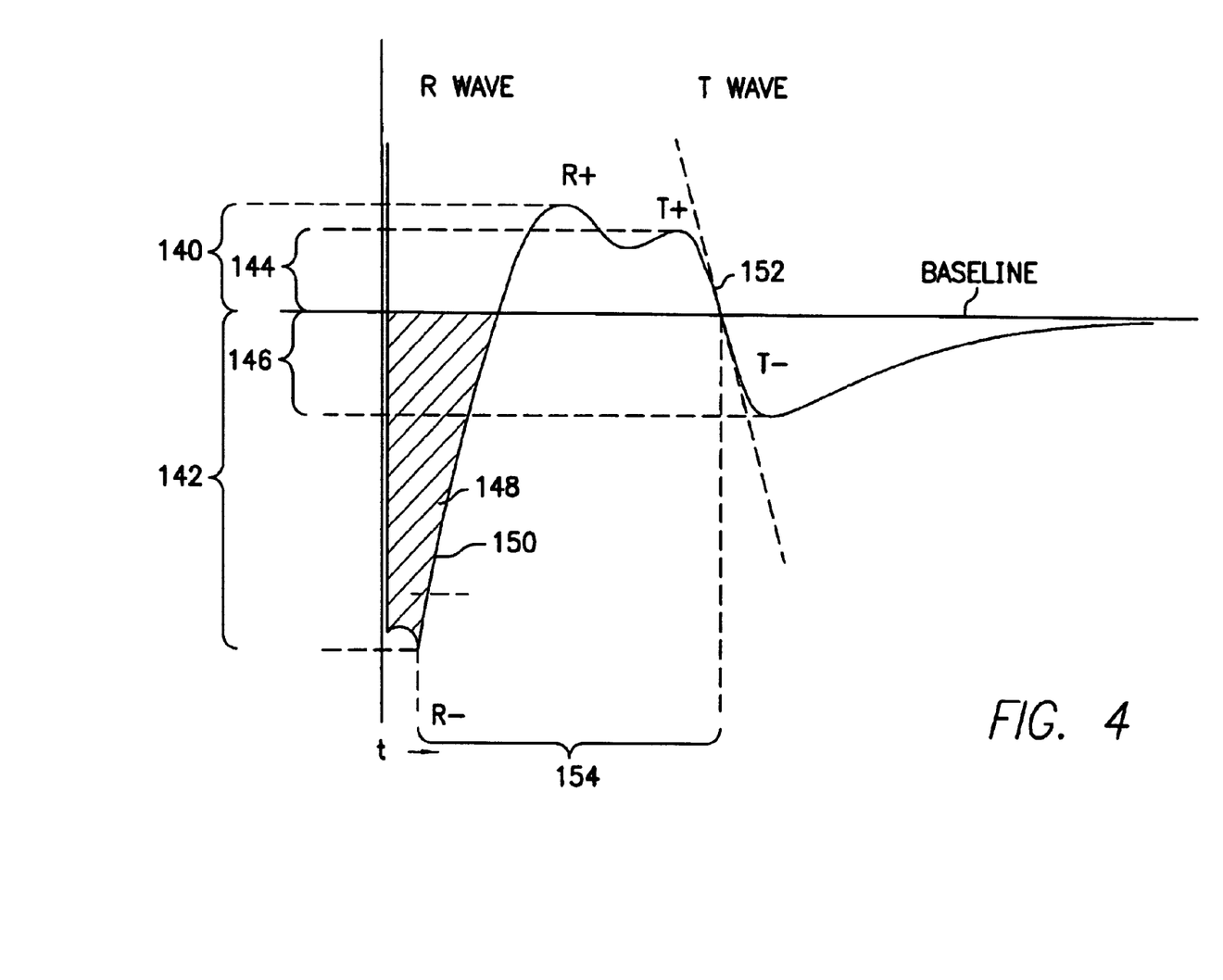
FIG. 4 is a waveform of an evoked response illustrating various fiduciary points and features which may be utilized in accordance with the present invention.

To enhance the ventricular electrogram, sensing electrode configurations are preferably used which encompass as much ventricular tissue as possible and as little atria tissue as possible. This will emphasize ventricular morphology features or characteristics such as Q waves, R waves, S waves, and T waves. Such sensing electrode configurations may be obtained by sensing between an electrode implanted in the right ventricle and another electrode implanted in the right ventricle, the right atrium, or the coronary sinus. Further, sensing may be performed between the conductive device enclosure and an electrode implanted in the right ventricle or between an electrode implanted in the right ventricle and an epicardial electrode on the left ventricle. Still further, suitable sensing may be obtained by sensing between a pair of left ventricular epicardial electrodes, or between a left ventricular epicardial electrode and the device conductive enclosure or an electrode implanted within the right ventricle, the coronary sinus, or the right atrium. The electrodes may be either the pace/sensing ring and tip type or less localized defibrillation coils. Any one of the foregoing sensing electrode configurations will provide a ventricular electrogram suitable to support the extraction and quantifying of ventricular deflection amplitudes and areas. Referring to FIG. 4, it illustrates an electrical waveform of a ventricular evoked response resulting from a ventricular pacing stimulus being applied to a ventricle of a heart. The evoked response waveform may be within an electrogram signal generated by the IEGM amplifier 85 (FIG. 2) or the sensing circuit 42 (FIG. 1).

The evoked response begins with an initial large negative deflection (the R wave) and then transitions into an extended positive deflection and plateau. The plateau ends with a transition to another smaller negative deflection (the T wave) and then returns to the baseline.

Morphology features or characteristics of the evoked response such as amplitudes, areas, timings, and rates of transitions (slopes) of the deflections, as well as the morphology as a whole, may all be extracted and quantified. The relative changes in the quantified value or values, when retained over time, will provide an indication of the progression or regression of heart disease. More specifically, and by way of example, a progression in heart disease would be indicated by a decrease in evoked response amplitudes, such as the R wave amplitudes 140 and 142, and the T wave amplitudes 144 and 146. Further, a progression in heart disease would also be indicated by a widening in the evoked response deflections. A progression in heart disease would also be indicated by a decrease in the area 148 of the evoked response R wave negative deflection below the baseline. Alternatively or in addition, a progression in heart disease would be indicated by a decrease in evoked response slew rates which may be observed by a decrease in slopes 150 and 152. As a last example, a progression in heart disease would be indicated by a shortening in evoked response intervals, such as the R to T interval 154.

Any one of the above noted evoked response morphology characteristics, mentioned as examples, when extracted, quantified, and monitored over time, would provide an indication of the progression of heart disease. Relative changes in these quantified values opposite to that described above would be indicative of a regression in heart disease.

The evaluation of any one of the morphology features or characteristics, or combinations thereof, is preferably implemented by the control circuits 22 of FIG. 1 or the control circuit 86 of FIG. 2. An evaluation method in accordance with the present invention, including extracting and quantifying a morphology characteristic for long term monitoring, is illustrated in the flow chart of FIG. 5.

Figure 5:
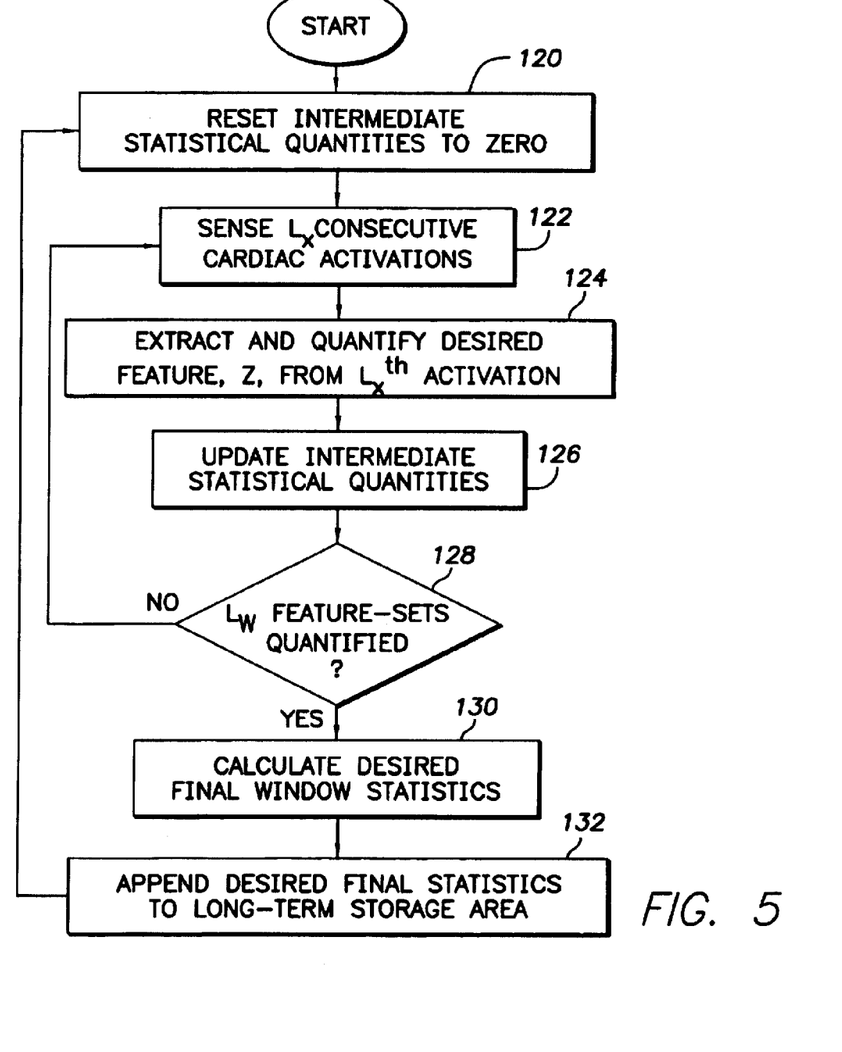
FIG. 5 is a flowchart that illustrates a method used to monitor progression or regression in heart disease in accordance with a preferred embodiment of the present invention.

The method illustrated in FIG. 5 initiates with an activity block 120 where intermediate statistical quantities from a prior long-term monitoring session are cleared from memory. For example, if the long-term final statistical quantity is a mean value, the intermediate quantity to be cleared may be a prior running sum.

The method then advances to activity block 122 wherein a predetermined number ($L_x$) of consecutive cardiac cycles are sensed. Since the purpose herein is to monitor a long-term trend, it would be most desirable to collect data from selected cardiac cycles. For example, it may be desired to collect data from every fiftieth cardiac cycle. Hence, $L_x$ would be equal to fifty.

After fifty cardiac cycles are sensed, in accordance with this preferred embodiment, the method advances to activity block 124 wherein the selected morphology characteristic or feature (Z) is extracted from the fiftieth cardiac cycle of the electrogram and quantified. Following activity block 124, the method advances to activity block 126 wherein the intermediate statistical quantity is updated in memory. Here, if the final statistic is a mean, the quantified featured statistic determined in activity block 124 is added to a running sum in activity block 126.

Following the updating in activity block 126, the method advances to decision block 128 wherein it is determined if a predetermined number ($L_w$) of intermediate statistics have been generated. For example, if one thousand intermediate statistics are to be collected before determining a final statistic, decision block 128 determines if activity steps 122 through 126 have been repeated one thousand times. If not, the method returns to activity block 122. If, however, all of the required data has been collected, the method advances to activity block 130 wherein the final statistic is calculated. Here, in this example, the intermediate running sum last updated in activity step 126 is divided by the number of intermediate statistical samples, one thousand, to calculate the final statistic. Once calculated, the final statistic is stored in memory in accordance with activity block 132 and the method returns.

As an alternative, the method need not immediately return to activity step 120. For example, it may be desired to determine a final statistic only once each day. Hence, the control circuits 22 and 86 of FIGS. 1 and 2, respectively, would place a pause in the return of 24 hours minus the execution time to calculate the final statistic. Alternatively, the control circuits may implement a 24-hour clock to activate activity step 120 every 24 hours. Other metrics on which to base pause duration are possible; for example, a pause of, e.g., 10,000 cardiac cycles.

The interval for gathering the data for calculating a final statistic may be referred to as a window. In the first example above, there is one window each day and the start of each window occurs 24 hours after the start of the immediately proceeding window. However, those skilled in the art may appreciate that more than one window may be running at any one time. Windows may be overlapped, be spaced apart, or immediately succeed each other. Furthermore, different morphological characteristics may be monitored in respective different overlapping windows.

Further, the final statistic may take many different forms. For example, it may be a mean as discussed above. It may be a variance, or an exponentially-weighted average (in which case intermediate statistical quantities need not be reset in activity block 120 of FIG. 5) or an out-of-bound count or percent.

As can thus be seen, over time, a wealth of morphology statistical data indicating progression or regression of heart disease will be available to a physician upon follow-up visits by the patient. The data merely need be downloaded from the implanted device to an external receiver, such as a programmer, for retrieval or display. The final statistical morphology data may be an evoked response amplitude, deflection width or area, slew rate, or interval, or intrinsic QRS complex duration, deflection areas, amplitudes, or polarity. The data may further relate to a template mismatch score. Relative changes in any one or all of the foregoing will provide an indication of the progression or regression of the heart disease.

Thus, an implantable cardiac device and method for detecting a progression or regression in heart disease over an extended time period are provided. One skilled in the art will appreciate that the present invention can be practiced by other than the described embodiments, which are presented for the purposes of illustration and not of limitation, and that the present invention is limited only by the claims that follow.

What is claimed is:

1. An implantable medical device for monitoring changes in heart disease, comprising:
    a sensing circuit that senses an intracardiac electrogram;
    a signal processing circuit, coupled to the sensing circuit, that determines amplitude, width and polarity from selected complexes within the intracardiac electrogram;
    a comparator that compares the amplitude, width and polarity of a current complex with the amplitude, width and polarity of a previous complex; and
    a controller that indicates relative changes between the current complex and the previous complex, wherein the relative changes correspond to changes in a progression or regression of the heart disease.

2. The implantable medical device recited in claim 1, wherein:
    the sensing circuit senses atrial complexes within the intracardiac electrogram; and
    the signal processing circuit determines amplitude, width and polarity from selected atrial complexes.

3. The implantable medical device recited in claim 1, wherein:
    the sensing circuit senses ventricular complexes within the intracardiac electrogram; and
    the signal processing circuit determines amplitude, width and polarity from selected ventricular complexes.

4. The implantable medical device recited in claim 1, wherein:
    the sensing circuit senses repolarization waveforms corresponding to T-wave complexes within the intracardiac electrogram; and
    the signal processing circuit determines amplitude, width and polarity from the repolarization waveforms.

5. The implantable medical device recited in claim 1, wherein:
    the sensing circuit senses intrinsic complexes within the intracardiac electrogram; and
    the comparator compares current intrinsic waveforms with previous intrinsic waveforms.

6. The implantable medical device recited in claim 1, wherein:
    the sensing circuit senses evoked complexes within the intracardiac electrogram; and
    the comparator compares current evoked waveforms with previous evoked waveforms.

7. The implantable medical device recited in claim 1, wherein:
    the controller determines a matching score based on the amplitude, width and polarity of the current complex to the previous complex, and further reports changes in the matching score, wherein the relative changes in the matching score correspond to changes in the progression or regression of the heart disease.

8. The implantable medical device recited in claim 1, wherein:
    the controller determines whether the current complex has exceeded an out-of-bound limit relative to the previous complex, wherein the out-of-bound limit corresponds to a change in the progression or regression of the heart disease.

9. The implantable medical device recited in claim 1, wherein:
    the signal processing circuit determines a template based on the amplitude, width and polarity of the selected complexes; and
    the comparator compares the template of the current complex with the template of the previous complex to produce a template matching score relative to the previous complex.

10. The implantable medical device recited in claim 1, wherein:
    the signal processing circuit measures the amplitude, width and polarity of a plurality of complexes and produces statistical values for the amplitude, width and polarity relating to the plurality of complexes.

11. The implantable medical device recited in claim 10, wherein:
    the signal processing circuit determines the statistical values based on at least one of a mean value, a variance value, an exponentially-weighted average, or a percentage value.

12. The implantable medical device recited in claim 1, wherein:
    the signal processing circuit determines an area based on the amplitude and width.

13. The implantable medical device recited in claim 1, wherein:
    the signal processing circuit further assigns a positive or a negative value associated with each selected complex.

14. The implantable medical device recited in claim 13, wherein:
    the controller indicates a relative change in the patient's heart disease when a change in the polarity of the current complex is detected.

15. An implantable medical device for monitoring changes in heart disease, comprising:
   means for measuring amplitude, width and polarity from selected complexes within an intracardiac electrogram;
   means for comparing the amplitude, width and polarity of a current complex with the amplitude, width and polarity of a previous complex; and
   control means for monitoring relative changes between the current complex and the previous complex, wherein the relative changes correspond to changes in the state of a patient's heart disease.

16. The implantable medical device recited in claim 15, wherein:
   the measuring means comprises means for detecting the selected complexes by detecting peak waveforms and for determining whether a peak waveform is one of P-wave, an R-wave or a T-wave.

17. The implantable medical device recited in claim 15, wherein:
   the comparing means comprises means for determining whether the current complex is either an intrinsic waveform or an evoked waveform.

18. The implantable medical device recited in claim 17, wherein:
   the comparing means comprises means for comparing current intrinsic waveforms with previous intrinsic waveforms, and means for comparing current evoked waveforms with previous evoked waveforms.

19. The implantable medical device recited in claim 15, wherein:
   the control means comprises means for determining a matching score based on the amplitude, width and polarity of the current complex to the previous complex, and further reports relative changes in the matching score, wherein the relative changes in the matching score correspond to changes in the progression or regression of the heart disease.

20. The implantable medical device recited in claim 15, wherein:
   the control means comprises means for determining an area based on the amplitude and width.

21. The implantable medical device recited in claim 15, wherein:
   the control means comprises means for determining whether the selected complex has a positive or a negative polarity associated therewith.

22. The implantable medical device recited in claim 21, wherein:
   the control means comprises means for indicating a relative change in the patient's heart disease when a change in the polarity of the selected complex is detected.

23. In an implantable medical device, a method for monitoring changes in heart disease, comprising:
   sensing selected complexes within an intracardiac electrogram;
   measuring an amplitude, width and polarity of each of the selected complexes;
   comparing the amplitude, width and polarity of a current complex with the amplitude, width and polarity of a previous complex to detect relative changes therebetween; and
   reporting the relative changes between the current complex and the previous complex, wherein the relative changes correspond to changes in the progression or regression of the heart disease.

24. The method in claim 23, wherein the measuring step comprises:
   detecting the selected complexes by detecting peak waveforms; and
   determining whether a peak waveform is one of a P-wave, an R-wave or a T-wave.

25. The method recited in claim 24, wherein:
   the determining step comprises determining whether the selected waveform is either an intrinsic waveform or an evoked waveform.

26. The method recited in claim 25, wherein:
   the comparing step further comprises comparing current intrinsic waveforms with a previous intrinsic waveforms, and comparing current evoked waveforms with previous evoked waveforms.

27. The method recited in claim 23, further comprising:
   determining a matching score based on the amplitude, width and polarity of the current complex relative to the previous complex; and
   reporting changes in the matching score, wherein the relative changes in the matching score correspond to changes in the progression or regression of the heart disease.

28. The method recited in claim 23, wherein:
   the comparing step comprises determining an area based on the amplitude and width, and comparing the area of the current complex with the area of the previous complex.

29. The method recited in claim 23, wherein:
   the comparing step comprises determining whether the selected complex has a positive or a negative polarity associated therewith, and comparing the polarity of the current complex with the previous complex.

30. The method recited in claim 29, wherein:
   the reporting step comprises reporting a relative change in the patient's heart disease when a change in the polarity of the selected complex is detected.

* * * * *